(12) United States Patent
Subramanian et al.

(10) Patent No.: US 9,301,921 B2
(45) Date of Patent: Apr. 5, 2016

(54) LAXATIVE GEL COMPOSITION

(71) Applicant: Gavis Pharmaceuticals, LLC, Somerset, NJ (US)

(72) Inventors: Veerappan Sellappan Subramanian, Mendham, NJ (US); Paranjothy Kanni, Mendham, NJ (US)

(73) Assignee: Gavis Pharmaceuticals, LLC, Somerset, NJ (US)

( * ) Notice: Subject to any disclaimer, the term of this patent is extended or adjusted under 35 U.S.C. 154(b) by 0 days.

(21) Appl. No.: 13/856,706

(22) Filed: Apr. 4, 2013

(65) Prior Publication Data

US 2013/0267607 A1 Oct. 10, 2013

Related U.S. Application Data

(60) Provisional application No. 61/620,707, filed on Apr. 5, 2012.

(51) Int. Cl.
*A61K 31/765* (2006.01)
*A61K 9/06* (2006.01)
*A61K 9/00* (2006.01)
*A61K 47/32* (2006.01)

(52) U.S. Cl.
CPC ............... *A61K 9/06* (2013.01); *A61K 9/0056* (2013.01); *A61K 31/765* (2013.01); *A61K 47/32* (2013.01)

(58) Field of Classification Search
CPC .................................................... A61K 31/765
See application file for complete search history.

(56) References Cited

U.S. PATENT DOCUMENTS 4,321,263 A * 3/1982 Powell et al. ............... 424/738
6,159,491 A * 12/2000 Durrani ....................... 424/430
2004/0115282 A1* 6/2004 Keiser et al. ................ 424/601

OTHER PUBLICATIONS

Nesba, "Is PEG (polyethylene glycol a more effective laxative than Lactulose in the treatment of a child who is constipated", 2007.*
"Patient Information Leaflet: MOVICOL", Product Label, Norgine Pty Limited, New South Wales, Australia, (Sep. 2010), 1 pg.

* cited by examiner

*Primary Examiner* — Zohreh Fay
(74) *Attorney, Agent, or Firm* — Schwegman Lundberg & Woessner, P.A.

(57) ABSTRACT

An edible, gel composition of a PEG and a gel forming agent wherein the composition is prepared by mixing together the PEG with gel forming agent to form the edible gel composition, and the edible gel composition has laxative properties.

3 Claims, No Drawings

LAXATIVE GEL COMPOSITION

CLAIM OF PRIORITY

This application claims the benefit of priority of U.S. Provisional Application Ser. No. 61/620,707, filed on Apr. 5, 2012, which application is herein incorporated by reference in its entirety.

BACKGROUND

Polyethylene glycol (PEG), particularly PEG 3350 is a known osmotic laxative. PEG 3350 is sold in US in laxative compositions which typically are to be combined with an aqueous medium. For example 17 g of PEG powder is dissolved in about 8 ounces of aqueous beverage and consumed to provide a laxative dosage. Examples of such products include Miralax® (MSD consumer care) and Gavilax® (Gavis Pharmaceuticals, NJ).

Formulation of PEG as a beverage or in an aqueous medium is inconvenient, unsatisfying and uncomfortable to the consumer. The aqueous formulation has an undesirable mouth-feel and can create a bloated, overwhelmed feeling in the consumer's stomach. The aqueous formulation is also not a drink that can be discretely consumed so that consumers typically use restrooms in which to mix and drink the formulation. This practice is uncomfortable, disagreeable and ill tasting. The discomfort and inconvenience leads to reduction of dose compliance of the product as directed. Thus, there is a need for more conveniently dosed polyethylene glycol.

While there are certain products, for example Movicol® (Norgine Ltd, Middx UB9 6NS, UK) that are sachets for combination with aqueous media, they contain in addition to polyethylene glycol, electrolytes such as sodium chloride, sodium bicarbonate and potassium chloride. These salts do not impart good taste and suffer from the same discomfort and inconvenience as an aqueous formulation containing only PEG.

Other laxatives formulated for oral consumption suffer from the same problems. All have disagreeable tastes, cause a bloated feeling in the stomach and require inconvenient mixing as aqueous formulations. Chief among these are the laxative preparations with water insoluble substances such as psyllium, bran husk, microcrystalline cellulose and the like. These all form gritty distasteful aqueous formulations that leave thick residue in the glass when drunk. Therefore, there is a need to provide a laxative dosage form that has a good taste and would enhance patient compliance.

SUMMARY OF INVENTION

The present invention is directed to a laxative based edible, gel composition. An aspect of the invention is the composition of such ingredients as a laxative, a gel forming agent and optional sweetening, coloring and flavoring agents.

A further aspect of the invention provides that the gel composition is formed as an edible gel by mixing the ingredients to form a fluid dispersion in water and to form a gel. In particular, and preferably, another aspect of the invention provides that the gel forming agent is first dispersed or otherwise converted into a flowable viscous to fluid state in water. The laxative is then combined with the fluid and mixed to form the gel dispersion. An aspect of invention is a sweetening agent, a flavor, and a coloring agent are added to the fluid dispersion. The fluid dispersion is added to containers preferably sized to produce one dose of laxative per container and allowed to cool to ambient temperature. Another aspect of the invention is to add sweetening agents, flavors and coloring agents before addition of laxative. Optionally, a preservative such as sodium benzoate, benzoic acid or parabens can be added. Preferably the preservatives after addition of laxative.

According to yet another aspect of the invention, the dispersion constituting the edible composition is gel at ambient temperature.

Additional aspects of the invention provide that the composition may optionally include sweeteners, flavoring agents, coloring agents and preservatives that can also be added to the composition as appropriate.

DETAILED DESCRIPTION

The objective was to develop a gel formulation that can be eaten with a spoon from a cup. The gel contains polyethylene glycol (PEG) of low (eg. 200) to high (eg. 40000) average molecular weight, preferably from about 200 to about 35000, more preferably from about 400 to about 10000, most preferably from about 400 to about 8000, especially most preferably about 400 to about 6000. PEG in this formulation acts as a laxative.

Several polymers such as sodium Carboxy Methyl cellulose sodium, Xanthan gum and carbopol were tried to form gel with PEG. With Carboxy methyl Cellulose Sodium, the gel separated into two layers. With Xanthan gum there was no gel formation at all. It is theorized that probably PEG itself is a water loving polymer and that could be the reason for the separation of the gel into two layers. Unexpectedly, carbopol polymer was very much compatible with PEG and formed a good gel. But even with Carbopol polymer, Citric acid and electrolytes were found to interfere in the gel formation. The striking observation was that Carbopol could form a good gel even at low concentration level in the formulation. It formed gels at less than 0.5 g and even up to levels below 0.05 g per dose of PEG of about 15 to 20 g. The process of preparation of the gel was very critical and needed much attention and care. It was found that Carbopol and PEG have to be added slowly with stirring. Also, it is preferable to add Carbopol and form dispersion before addition of PEG. Addition of PEG before Carbopol showed tendency of separation of PEG. It was also found that it is preferable to add sweetening agents, colorings agents and flavorings as appropriate, before addition of Carbopol for easier dispersion. Additionally, it was found surprisingly that addition of preservatives is preferable as the last step as it was found to interfere with gel formation if added earlier. RB-115-131 was chosen as the proto-type formula for further development.

TABLE 1

Gel formulations (Selection of polymers)

| | | Per Unit dose (gm) | | |
| --- | --- | --- | --- | --- |
| Item | Ingredients | RB115-117 | RB115-121 | RB115-118 |
| 1 | PEG 3350 | 17.000 | 17.000 | 17.000 |
| 2 | Purified water | 20.000 | 20.000 | 20.000 |
| 3 | Citric acid | 0.600 | — | — |
| 4 | Sucralose | 0.042 | — | 0.050 |
| 5 | Sod.carboxy methyl cellulose | 10.000 | — | — |
| 6 | Xanthan Gum | — | 4.000 | — |
| 7 | Carbopol 71G NF | — | — | 0.500 |
| 8 | Orange flavor | 0.100 | — | — |
| 9 | Orange color | 0.001 | — | — |

TABLE 1-continued

Gel formulations (Selection of polymers)

| | | Per Unit dose (gm) | | |
|---|---|---|---|---|
| Item | Ingredients | RB115-117 | RB115-121 | RB115-118 |
| 10 | Red # 40 | — | — | 0.001 |
| 11 | Strawberry Flavor | — | — | 0.100 |
| | Total Wt | 47.743 | 41.000 | 37.651 |
| | Comments | No gel formation with Sodium carboxy methyl cellulose | No gel formation with Xanthan gum | Good Gel forms with Carbopol. Carbopol has been selected for further experiments |

Procedure:
Purified water was taken and kept under stirring. Citric acid and Sucralose (if present in the formulation), color and flavors were added one by one and dissolved. Polymer (Sodium carboxy methyl cellulose or Xanthan gum or Carbopol) was added and dispersed. PEG 3350 was then added and dissolved.

TABLE 2

Gel formulations (effect of Citric acid and Electrolytes)

| | | Per Unit dose (gm) | |
|---|---|---|---|
| Item | Ingredients | RB115-119 | RB115-123 |
| 1 | PEG 3350 | 17.000 | 13.125 |
| 2 | Purified water | 22.000 | 20.000 |
| 3 | Citric acid | 0.500 | — |
| 4 | Sodium chloride | 0.100 | 0.351 |
| 5 | Pot.chloride | — | 0.049 |
| 6 | Sod.bi carbonate | — | 0.179 |
| 7 | Sucralose | 0.060 | — |
| 8 | Sugar | — | 5.000 |
| 9 | Carbopol 71G NF | 0.500 | 0.500 |
| 10 | Red # 40 | 0.001 | 0.001 |
| 11 | Strawberry Flavor | 0.150 | 0.200 |
| | Total Wt | 40.311 | 39.405 |
| | Comments | No gel formation | No gel formation |

Procedure:
Purified water was taken and kept under stirring. Citric acid, Sucralose or Sugar (if present in the formulation), 3 Electrolytes, color and flavors were added one by one and dissolved. Polymer carbopol was added and dispersed PEG 3350 was then added and dissolved.
No gel was formed. Citric acid lowerered pH less than 3.
Electrolytes also affect gel formation.

TABLE 3

Gel formulations with Carbopol Polymer (per unit dose gm)

| # | Ingredient | RB115-120 | RB115-122 | RB115-124 | RB115-125 | RB115-126 | RB115-127 | RB115-128 | RB115-129 |
|---|---|---|---|---|---|---|---|---|---|
| 1 | PEG 3350 | 17.000 | 17.000 | 17.000 | 17.000 | 17.000 | 17.000 | 17.000 | 17.000 |
| 2 | Purified water | 20.000 | 20.000 | 20.000 | 20.000 | 20.000 | 20.000 | 20.000 | 20.000 |
| 3 | Sucralose | 0.060 | — | — | — | — | — | — | — |
| 4 | Sugar | — | 5.000 | 5.000 | 5.000 | 5.000 | 5.000 | 5.000 | 5.000 |
| 5 | Carbopol 71G NF | 0.500 | 0.500 | 0.500 | 0.400 | 0.300 | 0.200 | 0.100 | 0.050 |
| 6 | Vanilla flavor | — | — | 0.200 | 0.200 | 0.200 | 0.200 | 0.200 | 0.200 |
| 7 | Red # 40 | 0.001 | 0.001 | — | — | — | — | — | — |
| 8 | Strawberry Flavor | 0.200 | 0.200 | — | — | — | — | — | — |
| | Total Wt | 37.761 | 42.701 | 42.700 | 42.600 | 42.500 | 42.500 | 42.500 | 42.250 |
| | Comments | Thick viscous Good gel pH 4.80 Not good taste | Thick viscous Good gel pH 4.80 Not good taste | Thick viscous Good gel pH 4.85 Not good taste | Thick viscous Good gel pH 4.90 Not good taste | Thick viscous Good gel pH 4.90 Moderate taste | Viscous Good gel pH 5.18 Good taste | Thin gel pH 5.47 Good taste | Thin gel pH 6.0 Good taste |

Procedure:
Purified water was taken and kept under stirring. Sucralose or Sugar (if present in the formulation) was added and dissolved. Color and flavor were added and dissolved. Polymer carbopol was added slowly over a period of 45 minutes and dispersed well. PEG 3350 was then added over a perod of 15 minutes and dissolved.
Considering the appearance, pH of the formulation and viscosity of the gel, Formulation RB-115-127 was selected for further experiments.

TABLE 1-continued

Gel formulations (Selection of polymers)

| | | Per Unit dose (gm) | | |
|---|---|---|---|---|
| Item | Ingredients | RB115-117 | RB115-121 | RB115-118 |

A good Gel was formed in case of the polymer carbopol and there was no gel formation with respect to other polymers tried.

TABLE 4

Gel with Strawberry Flavor RB-115-131

| # | Ingredients | 10 units (gm) |
|---|---|---|
| 1 | PEG 3350 | 170.000 |
| 2 | Purified Water | 200.000 |
| 3 | Carbopol 71G NF | 2.000 |
| 4 | Sugar | 60.000 |
| 5 | Red # 40 | 0.020 |
| 6 | Strawberry Flavor | 2.000 |
| | TOTAL WEIGHT | 434.020 |
| | Comments | A good palatable viscous gel. pH: 5.3 |

Procedure:
Purified water was taken and kept under stirring. Sugar was added and dissolved. Color and flavor were added and dissolved. Polymer carbopol was added slowly over a period of 45 minutes and dispersed well. PEG 3350 was then added over a period of 15 minutes and dissolved. Poured into containers.

TABLE 5

Gel with Strawberry Flavor RB-115-137

| # | Ingredients | 10 units (gm) |
|---|---|---|
| 1 | PEG 3350 | 170.000 |
| 2 | Purified Water | 200.000 |
| 3 | Carbopol 71G NF | 2.000 |
| 4 | Sugar | 60.000 |
| 5 | Purple color | 0.020 |
| 6 | Flavors | 2.000 |
| 7 | Sodium Benzoate | 1.000 |
|   | TOTAL WEIGHT | 434.020 |
|   | Comments | A good palatable viscous gel. pH: 5.3 |
|   | Observation | When sodium Benzoate was added before addition of Carbopol, good gel did not form. |

Procedure:

Same as 131. Sodium benzoate was added after addition of PEG.

The invention claimed is:

1. An edible laxative composition, consisting essentially of:
   a polyethylene glycol (PEG);
   carbopol;
   water; and
   optional sweetening, color and flavor agents;
   wherein the weight percentage of carbopol relative to the weight of PEG is in the range of from about 1.17% to about 1.2%, the weight percentage of carbopol to the combined weight of PEG and water is in the range of from about 0.5% to about 0.6%, the composition is free of citric acid and pharmaceutically acceptable electrolytes, the composition tastes good and the composition has the physical form of a viscous gel that is consumable by spoon and cup.

2. The composition according to claim 1 wherein the pH of the composition is in a range of from about 4.8 to about 6.0.

3. The composition according to claim 1 wherein the composition is free of pharmaceutically acceptable electrolytes which include potassium chloride, sodium chloride, sodium bicarbonate or any combination thereof.

* * * * *